United States Patent [19]

Norris et al.

[11] Patent Number: 5,519,049
[45] Date of Patent: May 21, 1996

[54] MACROLIDES FOR THE TREATMENT OF REVERSIBLE OBSTRUCTIVE AIRWAYS DISEASES

[75] Inventors: Alan A. Norris, Loughborough; Dale M. Jackson, Diseworth, both of England; Sohei Makino, Shimotsuga, Japan; Takeshi Fukuda; Ikuo Akutsu, both of Utsunomiya, Japan

[73] Assignees: Fisons plc, Ipswich, England; Fujisawa Pharmaceutical Company Limited, Osaka, Japan

[21] Appl. No.: 93,305

[22] Filed: Jul. 16, 1993

Related U.S. Application Data

[63] Continuation of Ser. No. 781,190, Jan. 27, 1992, abandoned.

[30] Foreign Application Priority Data

Jun. 6, 1989 [GB] United Kingdom ............ BA89/12935
Apr. 9, 1990 [JP] Japan ...................................... 2/96045

[51] Int. Cl.$^6$ .................................................. A61K 31/335
[52] U.S. Cl. ............................................ 514/449; 514/826
[58] Field of Search .................................. 514/291, 411, 514/449, 826

[56] References Cited

FOREIGN PATENT DOCUMENTS 0315978  5/1989  European Pat. Off. .
1-157913  6/1989  Japan .

OTHER PUBLICATIONS

Martindale, The Extra Pharmacopoeia, 28th ed. (1982) pp. 1445–1448.
Volk, Wesley A., Essentials of Medical Microbiology, 2nd edition (1982) pp. 202–203.
Remington's Pharmaceutical Sciences pp. 1314 and 1315, 17th Ed., 1985.
Sandoz "Azatricyclooctacosane . . . " Chem Abst 112(13):112071m (1989).
*Merck Manual* pp. 615, 627, 1982.
*Remington's* p. 1706, 1990.
*Current Therapy*, pp. 147–148, 1992.

*Primary Examiner*—Raymond Henley, III
*Attorney, Agent, or Firm*—Marshall, O'Toole, Gerstein, Murray & Borun

[57] ABSTRACT

Compositions comprising certain macrolides are disclosed which are useful in methods for the treatment of reversible obstructive airway diseases, particularly asthma.

11 Claims, No Drawings

MACROLIDES FOR THE TREATMENT OF REVERSIBLE OBSTRUCTIVE AIRWAYS DISEASES

This is a continuation of U.S. application Ser. No. 07/781,190, filed Jan. 27, 1992, now abandoned.

This invention relates to a novel treatment of reversible obstructive airways disease, more particularly to the use of macrocyclic compounds in the treatment of reversible obstructive airways disease, and to compositions containing such compounds.

European Patent Application 184162 (to Fujisawa Pharmaceuticals Co. Ltd.) discloses several macrolides (numbered FR-900506, FR-900520, FR-900523 and FR-900525) and derivatives thereof which are isolated from microorganisms belonging to the genus Streptomyces. The macrolides are indicated as immunosuppressive agents. European Patent Application 323042 (to Fisons plc) discloses many macrolides which may be derived from those disclosed in European Patent Application 184162. Again, the compounds are primarily indicated as immunosuppressive agents. European Patent Applications 349049 and 349061 (to Merck & Co. Inc., published after the priority date of the present invention) disclose the dihydroxycyclohexyl derivatives of FR-900506 and FR-900520 respectively and indicate them primarily as immunosuppressive agents. None of the documents mentioned above discloses or suggests the use of the compounds disclosed in the treatment of reversible obstructive airways disease.

We have now surprisingly found that a number of macrocyclic compounds, including some of those disclosed in the documents mentioned above (which are herein incorporated by reference), are efficacious in the treatment of reversible obstructive airways disease.

Thus, according to the present invention, we provide the use of a compound of formula I,

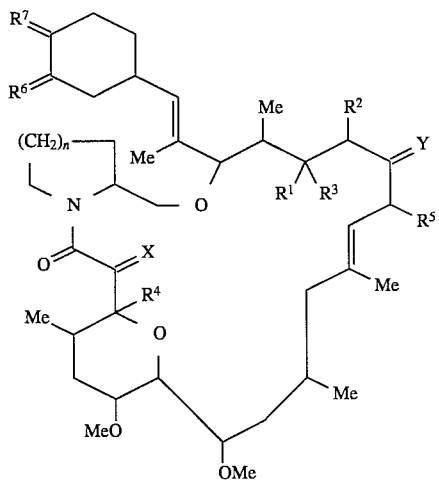

wherein $R^1$ and $R^2$ together represent two vicinal hydrogen atoms, or form a second bond between the vicinal carbon atoms to which they are attached;
$R^3$ represents H, OH, alkoxy or protected hydroxy;
$R^4$ represents OH;
$R^5$ represents H, alkyl or alkenyl;
$R^6$ and $R^7$ independently represent O, (H,OH), (H,protected hydroxy) or (H,alkoxy);
X and Y independently represent O, (H,OH) or (H,H);
n is 1 or 2;
or a pharmaceutically acceptable derivative thereof; as active ingredient in the manufacture of a medicament for the treatment of reversible obstructive airways disease.

European Patent Application No 327009 (to Fujisawa Pharmaceuticals Co. Ltd., published after the priority date of the present invention) discloses the use of two compounds and their derivatives in the treatment of asthma. Characterizing data for the compounds is given, but their structure is not apparent. Should the compounds of European Patent Application No 327009 fall within the scope of formula I above, they are excluded from the present invention.

Preferably, when $R^3$, $R^5$, $R^6$ and $R^7$ comprise carbon-containing groups, those groups contain up to 10 carbon atoms, more preferably from 1 to 6, e.g. methyl or methoxy.

$R^5$ is preferably allyl (i.e. prop-2-enyl), propyl, ethyl or methyl.

Preferably, n is 2.

Desirably, at least one of $R^6$ and $R^7$ represents (H,OH).

We prefer Y to represent O.

The present invention provides the use of all stereoisomers of the compounds of formula I. However, we prefer the compounds of formula I to have the stereochemistry shown in formula Ia:

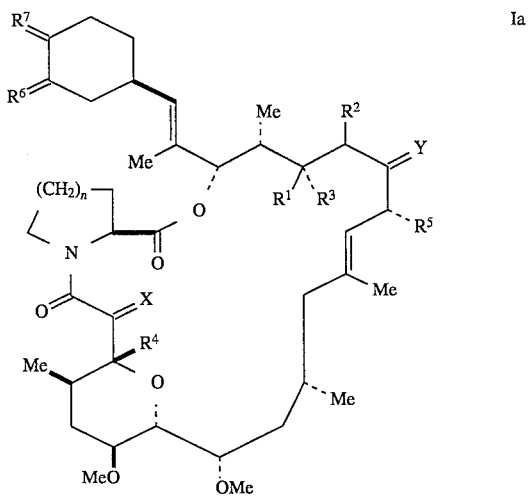

By the term "protected hydroxy" we mean a group which may be treated so as to yield a hydroxy group. Examples of such groups include an oxygen atom bonded to a protecting group selected from the following:

a) 1-(alkyl C1 to C6 thio)alkyl C1 to C6 such as alkyl C1 to C6 thiomethyl (e.g. methyl thiomethyl, ethylthiomethyl, propylthiomethyl, isopropylthiomethyl, butylthiomethyl, isobutylthiomethyl, hexylthiomethyl), preferably alkyl C1 to C4 thiomethyl and most preferably methylthiomethyl;

b) trisubstituted silyl such as tri(alkyl C1 to C6)silyl (e.g. trimethylsilyl, triethylsilyl, tributylsilyl, 'butyldimethylsilyl, tri-'butylsilyl) (alkyl C1 to C6)diarylsilyl (e.g. methyldiphenylsilyl, ethyldiphenylsilyl, propyldiphenylsilyl, 'butyldiphenylsilyl), preferably tri(alkyl C1 to C6)silyl and (alkyl C1 to C6)diphenylsilyl, most preferably 'butyldimethylsilyl and 'butyldiphenylsilyl; and c) acyl such as aliphatic acyl, aromatic acyl and aliphatic acyl substituted with aromatic groups, which are derived from carboxylic, sulphonic and carbamic acids.

Preferred protected hydroxy groups that may be mentioned include trialkylsilyloxy groups, for example 'butyldimethylsilyloxy.

Further protecting groups and methods for the introduction and removal of protecting groups are described in 'Protective Groups in Organic Chemistry', ed: J. W. F. McOmie, Plenum Press (1973), and 'Protective Groups in Organic Synthesis', T. W. Greene, Wiley-Interscience (1981).

Pharmaceutically acceptable derivatives of compounds of formula I include esters formed between hydroxy groups and carboxylic acids, and salts (for example alkali metal salts) formed with any acidic groups which may be present.

Specific compounds of formula I which may be mentioned include:

17-allyl-1,14-dihydroxy-12-12-(4-hydroxy-3-methoxycyclohexyl)-1-methylvinyl] -23,25-dimethoxy-13,19,21,27-tetramethyl-11,28-dioxa-4-azatricyclo [22.3.1.0$^{4,9}$]octacos-18-ene-2,3,10,16-tetraone, 17-ethyl-1,14-dihydroxy-12-[2-(4-hydroxy-3-methoxycyclohexyl)-1-methylvinyl] -23,25-dimethoxy-13,19,21,27-tetramethyl-11,28-dioxa-4-azatricyclo [22.3.1.0$^{4,9}$]octacos-18-ene-2,3,10,16-tetraone, 17-allyl-1,14-dihydroxy-12-[2-(3,4-dihydroxycyclohexyl) -1-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone, 17-ethyl-1,14-dihydroxy-12-[2-(3,4-dihydroxycyclohexyl)-1-methylvinyl] -23,25-dimethoxy-13,19,21,27-tetramethyl11,28-dioxatricyclo[22.3.1.0$^{4,9}$] octacos-18-ene2,3,10,16-tetraone, 17-propyl-1-hydroxy-12-[2 -(4-hydroxy-3-methoxycyclohexyl)-1-methylvinyl] -23,25-dimethoxy-13,19,21,27-tetramethyl-11,28-dioxa-4-azatricyclo 22.3.1.0$^{4,9}$]octacos-18-ene-2,3,10,16-tetraone, 17-allyl-1,2,14-trihydroxy-12-[2-(4-hydroxy-3-methoxycyclohexyl)-1-methylvinyl] -23,25-dimethoxy13,19,21,27-tetramethyl-11,28-dioxa-4-azatricyclo 22.3.1.0$^{4,9}$]octacos-18-ene-3,10,16-trione, or 17-allyl-1-hydroxy-12-[2-(4-hydroxy-3-methoxycyclohexyl)-1-methylvinyl] -23,25-dimethoxy13,19,21,27-tetramethyl-11,28-dioxa-4-azatricyclo [22.3.1.0$^{4,9}$]octacos-18-ene-2,3,10,16-tetraone.

The term "treatment" as used herein includes prophylaxis as well as relieving the symptoms of disease.

The term "reversible obstructive airways disease" will be well understood by those skilled in the art to include conditions such as asthma, including bronchial asthma, allergic asthma, intrinsic asthma, extrinsic asthma and dust asthma, particularly chronic or inveterate asthma (for example late asthma and airway hyper-responsiveness); bronchitis and the like, especially irriatative bronchitis caused by dust, chemical fumes, smoke, and other agents [see for example U.K. Patent No. 2022078 and Brit J Pharmac (1987), 24, 4983-501]. Of particular interest is asthma.

Administration of the active ingredient may be topical (for example by inhalation to the lung), or systemic (for example by oral administration to the gastrointestinal tract).

Dealing first with topical administration, those compounds of formula I which are solids at room temperature may be inhaled as a dry powder which may be pressurized or non-pressurized. In non-pressurized powder compositions, the active ingredient in finely divided form may be used in admixture with a larger sized pharmaceutically acceptable inert carrier comprising particles, e.g. of up to 100μm diameter. Suitable inert carriers include sugars, for example crystalline lactose. Desirably, at least 95% by weight of the particles of the active ingredient have an effective particle size in the range 0.01 to 10μm.

By providing a large proportion of fine particles of active ingredient the invention enables a lower dosage of drug to be administered and/or for an equivalent amount of drug to produce a greater or longer lasting effect, because fine particles are more likely to penetrate into the deeper regions of the human airways.

The finely divided active ingredient may be made by grinding or milling and is preferably dried thoroughly before formulation.

Non-pressurized powder compositions preferably contain from 0.2 to 5% by weight, more preferably from 0.5 to 2.5% by weight, and particularly from 1 to 1.5% by weight of the active ingredient, and from 95 to 99.8% by weight, more especially from 98.5 to 99% by weight of the carrier.

The composition may alternatively be pressurized and contain a compressed gas, e.g. nitrogen, or a liquefied gas propellant.

In pressurized compositions, the active ingredient is preferably finely divided, e.g. having a mass median diameter in the range 0.01 to 10 μm (and these finely divided forms of the active ingredient are a feature of the invention). We particularly prefer the active ingredient to have a mass median diameter of less than 4 μm and especially of less than 3.0 μm and most preferably of less than 2.8 μm. We also prefer not more than 5% by weight of the particles to have a diameter of greater than 10 μm, and more preferably not less than 90% by weight of the particles to have a diameter of less than 6 μm.

We prefer pressurized compositions to contain from 0.01 to 5%, more preferably from 0.1 to 1%, and most preferably from 0.1 to 0.5% of finely divided active ingredient.

By "mass median diameter" we mean that half the particulate mass is in particles of lesser diameter and half in particles of greater diameter than the specified mass median diameter. The mass median diameter is essentially a Stokes diameter and may be determined using a Joyce Loebl sedimentation disc centrifuge either in a two layer or line start photometric mode [Bagness J and Ottaway A; Proc Soc Analyt Chem, Part 4, Vol 9; (1972) pp83–86].

The liquefied propellant medium, and indeed the total composition, is preferably such that the active ingredient does not dissolve therein to any substantial extent.

The liquefied propellant is preferably a gas at room temperature (20° C.) and atmospheric pressure, i.e. it should have a boiling point below 20° C. at atmospheric pressure. The liquefied propellant should also be non-toxic. Among the suitable liquefied propellants which may be employed are dimethyl ether and alkanes containing up to five carbon atoms, e.g. butane or pentane, or a lower alkyl chloride, e.g. methyl, ethyl or propyl chlorides. The most suitable liquefied propellants are the fluorinated and fluorochlorinated lower alkanes such as are sold under the Registered Trade Mark [FREON] (the use of the latter type of propellants is a matter of current concern, and they may be replaced by a suitable substitute when such is available). Mixtures of the above mentioned propellants may suitably be employed. Examples of these propellants are:

dichlorodifluoromethane ('Propellant 12'),
1,2-dichlorotetrafluoroethane ('Propellant 114')
trichloromonofluoromethane ('Propellant 11'),
dichloromonofluoromethane ('Propellant 21')
monochlorodifluoromethane ('Propellant 22')
trichlorotrifluoroethane ('Propellant 113'), and
monochlorotrifluoromethane ('Propellant 13').

Propellants with improved vapor pressure characteristics may be obtained by using certain mixtures of these compounds, e.g. propellant 11 with propellant 12, or propellant 12 with propellant 114. For example, propellant 12, which has a vapor pressure of about 570 kPa (absolute) at 20° C. and propellant 114, with a vapor pressure of about 180 kPa (absolute) at 20° C., may be mixed in various proportions to form a propellant having a desired intermediate vapor pressure. We prefer compositions which do not contain trichloromonofluoromethane.

It is desirable that the vapor pressure of the propellant employed be between 380 and 500, and preferably between 410 and 470 kPa (absolute) at 20° C. Such a propellant mixture is usable safely with metal containers. Other mixtures of propellant 12 with propellant 114, or of propellant 12 with propellant 11, or of propellant 12 with propellant 11 and propellant 114 with absolute vapor pressures at 20° C. in the range 230 to 380 kPa are usable safely with specially reinforced glass containers.

The pressurized composition may also contain a surface active agent.. The surface active agent may be a liquid or solid non-ionic surface active agent or may be a solid anionic surface active agent. It is preferred to use the solid anionic surface active agent in the form of the sodium salt.

The preferred solid anionic surface active agent is sodium dioctyl-sulphosuccinate.

The amount of the surface active agent required is related to the solids content of the suspension and to the particle size of the solids. In general it is only necessary to use 5–15%, and preferably 5–8%, of the solid anionic surface active agent by weight of the solids content of the suspension.

When a liquid, non-ionic surface-active agent is employed it should have a hydrophile-lipophile balance (HLB) ratio of less than 10. The HLB ratio is an empirical number which provides a guide to the surface-active properties of a surface-active agent. The lower the HLB ratio, the more lipophilic is the agent, and conversely, the higher the HLB ratio, the more hydrophilic is the agent. The HLB ratio is well known and understood by the colloid chemist and its method of determination is described by W C Griffin in the Journal of the Society of Cosmetic Chemists, Vol 1, No 5, pages 311–326 (1949). Preferably the surface-active agent employed should have an HLB ratio of 1 to 5. It is possible to employ mixtures of surface-active agents, the mixture having an HLB ratio within the prescribed range.

Those surface-active agents which are soluble or dispersible in the propellant are effective. The more propellant-soluble surface-active agents are the most effective.

We prefer the liquid non-ionic surface-active agent to comprise from 0.1 to 2%, and more preferably from 0.2 to 1%, by weight of the total composition. Such compositions tend to be more physically stable on storage.

Among the liquid non-ionic surface-active agents which may be employed are the esters or partial esters of fatty acids containing from 6 to 22 carbon atoms, such as caproic, octoic, lauric, palmitic, stearic, linoleic, linolenic, oleo-stearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the Registered Trade Mark 'SPAN') and the polyoxyethylene and polyoxypropylene derivatives of these esters. Mixed esters, such as mixed or natural glycerides, may be employed. The preferred liquid non-ionic surface-active agents are the oleates of sorbitan, e.g. those sold under the Registered Trade Marks ARLACEL C (Sorbitan sesquioleate), SPAN 80 (Sorbitan monooleate) and SPAN 85 (Sorbitan trioleate). Specific examples of other liquid non-ionic surface-active agents which may be employed are sorbitan monolaurate, polyoxyethylene sorbitol tetraoleate, polyoxyethylene sorbitol pentaoleate, and polyoxypropylene mannitol dioleate.

We particularly prefer compositions containing a sorbitan or sorbitol ester, e.g. sorbitan trioleate, in a mixture of propellants 12 and 114. We prefer the ratio of propellant 12 to 114 to be in the range from 2:1 to 1:1, and preferably about 1.5:1 by weight, i.e. we prefer an excess of propellant 12 over propellant 114.

We prefer packages containing from about 8 to 30 ml of composition, e.g. a conventional aerosol pressure pack of 10 ml. The pack preferably has a valve adapted to deliver unit dosages of between 0.025 and 0.25 ml, and preferably 0.05 or 0.1 ml, of composition. We prefer the valve to deliver from 2 to 0.02 mg, for example 0.2 mg of active ingredient and unit doses of these quantities of the drug are provided.

A suitable dose for administration by inhalation is in the range from 0.001 to 0.1 $mgkg^{-1}day^{-1}$, and preferably 0.01 $mgkg^{-1}day^{-1}$.

The pressurized compositions of the invention may be made by mixing the various components at a temperature and pressure at which the propellant is in the liquid phase and the active ingredient is in the solid phase.

Thus, according to a second aspect of the present invention, there is provided a method of preparing a pharmaceutical pressurized aerosol composition comprising a compound of formula I, as defined above, or a pharmaceutically acceptable derivative thereof, which comprises mixing the finely divided active ingredient with a pharmaceutically acceptable aerosol propellant.

We further provide a pharmaceutical pressurized aerosol composition comprising a compound of formula I as defined above, or a pharmaceutically acceptable derivative thereof, and a pharmaceutically acceptable aerosol propellant.

In producing the pressurized compositions and packages of the invention, a container equipped with a valve is filled with a propellant containing the finely-divided active ingredient in suspension. A container may first be charged with a weighed amount of dry active ingredient which has been ground to a predetermined particle size, or with a slurry of powder in the cooled liquid propellant. A container may also be filled by introducing powder and propellant by the normal cold filling method, or a slurry of the powder in that component of the propellant which boils above room temperature may be placed in the container, the valve sealed in place, and the balance of the propellant may be introduced by pressure filling through the valve nozzle. As a further alternative a bulk of the total composition may be made and portions of this bulk composition may be filled into the container through the valve. Throughout the preparation of the product care is desirably exercised to minimize the absorption of moisture. On operating the valve, the powder will be dispensed in a stream of propellant, which will vaporize providing an aerosol of dry powder.

Turning now to systemic administration, the active ingredient may be formulated together with known adjuvants, diluents or carriers using conventional techniques to produce tablets or capsules for oral administration to the gastrointestinal tract. Suitable doses for such oral administration are in the range from 0.003 to 0.3 $mgkg^{-1}day^{-1}$, for example 0.03 $mgkg^{-1}day^{-1}$.

According to a third aspect of the present invention, there is provided a method of treatment of reversible obstructive airways disease, which method comprises administration of a therapeutically effective amount of a compound of formula I as defined above, or a pharmaceutically acceptable derivative thereof, to a person suffering from, or susceptible to, the disease.

The method of treatment according to the invention has the advantage that the compounds of formula I as defined above, or pharmaceutically acceptable derivatives thereof, are more efficacious, less toxic, are longer acting, have a broader range of activity, are more potent, produce fewer side effects, are more easily absorbed or have other useful pharmacological properties, than compounds previously used in the treatment of reversible obstructive airways disease.

The dosage to be administered will of course vary with the particular active ingredient, the condition to be treated and with its severity.

It is preferred that the dose be such as to give a sustained rather than a transitory action.

The active ingredient may be administered as divided doses from 1 to 6, and preferably 2 to 4, times per day.

The invention is illustrated, but in no way limited by, the following Examples.

Example A

Pressurized aerosol composition

| Ingredients | |
| --- | --- |
| 17-propyl-1-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (mass median diameter less than 3 microns) | 0.054 |
| Sorbitan trioleate | 0.091 |
| Propellant 114 | 7.099 |
| Propellant 12 | 10.649 |
| | 17.893 |

Method: the sorbitan ester is dispersed in up to half the propellant 12 at $-40°$ C. while stirring with a high dispersion mixer. The finely divided active ingredient is added to the resulting dispersion and disperses in it. The balance of the propellant 12 is then added at $-50°$ C., followed by the propellant 114 also cooled to $-50°$ C. The resulting mixtures are then filled into vials onto which valves, e.g. metering valves, are subsequently crimped.

Example B

Pressurized aerosol Composition containing FR-900506

| Ingredients | |
| --- | --- |
| FR-900506 (mass median diameter less than 3 microns) | 0.054 |
| Sorbitan trioleate | 0.091 |
| Propellant 114 | 7.099 |
| Propellant 12 | 10.649 |
| | 17.893 |

The pressurized aerosol composition was prepared following the method of Example A.

Example C

Assay for inhibitory activity against respiratory resistance and antigen-induced bronchial hyper-responsiveness Method (1) Preparation of inhalation-sensitized guinea pigs Male Hartley guinea pigs (weighing about 300 g) were each placed in a plastic inhalation chamber. Using an ultrasonic nebulizer (NEU10B, Omron Corporation), an aerosolized solution of ovalbumin in physiological saline (10 mgml$^{-1}$) was introduced into the chamber for 10 minutes daily for 10 consecutive days to effect sensitization. The animals were used in the experiments 5 days after establishment of sensitization.

(2) Pretreatment with FR-900506

During the period from the first day of sensitization to the day before an antigen challenge, the animals were orally treated with a 1 mgml$^{-1}$ solution of FR-900506 (in ethanol/olive oil [2:78 v/v]) every other day. Control animals received the ethanol/olive oil vehicle alone in the same manner.

(3) Experimental schedule

The experimental period was 5 days from day 1 to day 5, and the inhalation challenge with the antigen was given on day 2.

On day 1, and 30 minutes before antigen inhalation challenge on day 2, metopirone (an endogenous cortisol synthesis inhibitor) was intravenously administered (10 mgkg$^{-1}$). So that the animals could tolerate the antigen at comparatively high concentrations, chlorpheniramine maleate, an antihistaminic, was intraperitoneally administered (10 mgkg$^{-1}$) following the second dose of metopirone. After the pretreatment discussed above, each guinea pig was transferred to an animal box connected to an oscillator and fixed therein with its head projecting out. The head was then covered with an aerochamber communicating with a Devilvis 646 nebulizer.

(4) Assay for respiratory resistance

The assay for respiratory resistance was performed by the oscillation method of Mead et al with some modification (Allergy, 37, 10, 980–991, 1988). The antigen inhalation challenge was made by nebulizing a saline solution of ovalbumin (20 mgml$^{-1}$) with 5 l min$^{-1}$ of air and causing the animals to inhale for 1 minute. The results are shown in Table 1.

(5) Assay for antigen-induced bronchial hyper-responsiveness to acetylcholine

Guinea pigs prepared by the method described above were placed in an animal box as described above and the baseline respiratory resistance was measured. The animals were then caused to inhale a nebulized saline solution of acetylcholine (in an ascending concentration series of 156 to 5000 µgml$^{-1}$) for 1 minute at each concentration until the respiratory resistance was increased to twice the baseline value. From the concentration-resistance curve constructed from the acetylcholine concentration and respiratory resistance data, the acetylcholine concentration necessary for increasing the respiratory resistance to twice the baseline value [i.e. PC$_{200}$-Ach (µgml$^{-1}$)] was calculated. The results are shown in Table 2.

(6) Analysis of data

The results are expressed as mean ±SEM. Student's t-test was used as the test for significant difference.

RESULTS

TABLE 1

| Inhibitory effect of FR-900506 on respiratory resistance (%) | | |
| --- | --- | --- |
| Time after | Change in respiratory resistance (%) | |
| antigen inhalation challenge (hrs) | Control (n = 15) | FR-900506 treated (n = 7) |
| 3 | 131 ± 10 | *95 ± 7.3 |

TABLE 1-continued

Inhibitory effect of FR-900506 on respiratory resistance (%)

| Time after antigen inhalation challenge (hrs) | Change in respiratory resistance (%) | |
|---|---|---|
| | Control (n = 15) | FR-900506 treated (n = 7) |
| 6 | 185 ± 18 | *115 ± 9.5 |
| 9 | 152 ± 14 | *108 ± 4.3 |

*P < 0.05

Change in respiratory resistance (%) =
$$\frac{\text{Respiratory resistance after challenge}}{\text{Respiratory resistance before challenge}} \times 100\%$$

TABLE 2

Inhibitory effect of FR-900506 on antigen induced hyper-responsiveness to acetylcholine

| Time after antigen inhalation challenge (hrs) | $PC_{200}$-Ach (µgml$^{-1}$) | | |
|---|---|---|---|
| | Control (n = 15) | | FR-900506 treated (n = 7) |
| Before challenge | 1866 ± 313 | | 1192 ± 358 |
| | * | NS | NS |
| 24 | 553 ± 80 | NS | 883 ± 191 |
| | * | | NS |
| 72 | 1353 ± 196 | | 1492 ± 354 |

*P < 0.001
NS = no significant difference

The results indicate that the compounds of formula J are likely to be most efficacious in the treatment of reversible obstructive airways disease.

Example D

Acute toxicity of FR-990506

An acute intraperitoneal toxicity study of FR-900506 in ddy mice revealed no deaths at 100 mgkg$^{-1}$.

We claim:

1. A pharmaceutical pressurized aerosol composition, which is adapted for inhalation to the lungs, said composition comprising a compound of formula I,

[Structure I]

wherein $R^1$ and $R^2$ together represent two vicinal hydrogen atoms, or form a second bond between the vicinal carbon atoms to which they are attached;

$R^3$ represents H, OH, alkoxy. or protected hydroxy;

$R^4$ represents OH;

$R^5$ represents allyl, propyl, ethyl, or methyl;

$R^6$ and $R^7$ independently represent O, (H, OH), (H, protected hydroxy) or (H, alkoxy);

X and Y independently represent O or (H, OH); and n is 1 or 2, and a pharmaceutically acceptable aerosol propellant.

2. A pharmaceutical nonpressurized powder composition which is adapted for inhalation to the lungs, said composition comprising a compound of formula I

[Structure I]

wherein $R^1$ and $R^2$ together represent two vicinal hydrogen atoms, of form a second bond between the vicinal carbon atoms to which they are attached;

$R^3$ represents H, OH, alkoxy or protected hydroxy;

$R^4$ represents OH;

$R^5$ represents allyl, propyl ethyl, or methyl;

$R^6$ and $R^7$ independently represent O, (H, OH), (H protected hydroxy) or (H, alkoxy);

X and Y independently represent O or (H, OH); and n is 1 or 2, and crystalline lactose.

3. A method of treatment of asthma which comprises administration to the lung or gastrointestinal tract of a person in need of such treatment, of a therapeutically effective amount of a compound of formula I,

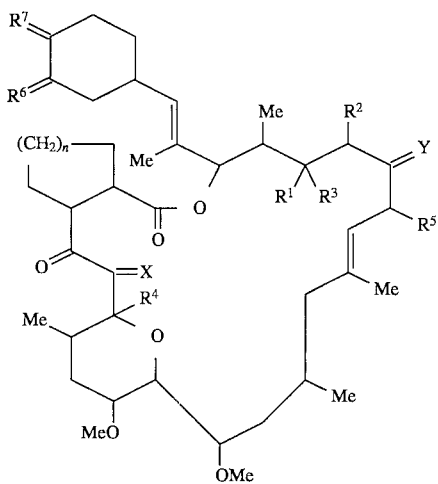

wherein $R^1$ and $R^2$ together represent two vicinal hydrogen atoms, or form a second bond between the vicinal carbon atoms to which they are attached;

$R^3$ represents H, OH, alkoxy or protected hydroxy;

$R^4$ represents OH;

$R^5$ represents allyl, propyl, ethyl, or methyl;

$R^6$ and $R^7$ independently represent O, (H, OH), (H, protected hydroxy) or (H, alkoxy);

X and Y independently represent O or (H, OH); and n is 1 or 2.

4. The method according to claim 3 wherein at least one of $R^6$ and $R^7$ represents (H, OH).

5. The method according to claim 3 wherein Y represents O.

6. The method according to claim 3 wherein n is 2.

7. The method according to claim 3 wherein the compound of formula I is:

17-ethyl-1,14-dihydroxy-12-[2-(4-hydroxy-3-methoxycyclohexyl)-1-methylvinyl] -23,25-dimethoxy-13,19,21,27-tetramethyl-11,28-dioxa-4-azatricyclo [22.3.1.0$^{4,9}$]octacos-18-ene-2,3,10,16-tetraone, 17-allyl-1,14-dihydroxy-12-[2-(3,4-dihydroxycyclohexyl)-1-methylvinyl] -23,25-dimethoxy-13,19,21,27-tetramethyl-11,28-dioxa-4azatricyclo[ [22.3.1.0$^{4,9}$octacos-18-ene-2,3,10,16-tetraone, 17-ethyl-1,14-dihydroxy-12-[2-(3,4-dihydroxycyclohexyl)-1-methylvinyl] -23,25-dimethoxy-13,19,21,27-tetramethyl-11,28-dioxa-4-azatricyclo [22.3.1.0$^{4,9}$]octacos-18-ene-2,3,10,16-tetraone, 17-propyl-1-hydroxy-12-23,25-dimethoxy-13,19,21,27-tetramethyl-11,28-dioxa-4-azatricyclo [22.3.1.0$^{4,9}$]octacos-18-ene-2,3,10,16-tetraone, 17-ally-1,2,14-trihydroxy-12-[2-(4-hydroxy-3-methoxycyclohexyl)-1-methylvinyl] -23,25-dimethoxy-13,19, 21,27-tetramethyl-11,28-dioxa-4-azatricyclo [22.3.1.0$^{4,9}$]octacos-18-ene-3,10,16-trione, or 17-allyl-1-hydroxy-12-[2-(4-hydroxy-3-methoxycyclohexyl)-1-methylvinyl] -23,25-dimethoxy-13,19,21,27-tetramethyl-11,28-dioxa-4-azatricyclo[22.3.1.0$^{4,9}$] octacos-18-ene-2,3,10,16-tetraone.

8. The method according to claim 3 wherein the compound of formula I is:

17-allyl-1,14-dihydroxy-12-[2-(4-hydroxy-3-methoxycyclohexyl)-1-methylvinyl] -23,25-dimethoxy-13,19,21, 27-tetramethyl-11,28-dioxa-4-azatricyclo [22.3.1.0$^{4,9}$] octacos-18-ene-2,3,10,16-tetraone.

9. The method according to claim 3, wherein the compound of formula I is administered by inhalation to the lung.

10. The method according to claim 3, wherein the compound of formula I is administered orally to the gastrointestinal tract.

11. A method according to claim 11 wherein the compound of formula I is administered by inhalation to the lung as a dry powder.

* * * * *

UNITED STATES PATENT AND TRADEMARK OFFICE
CERTIFICATE OF CORRECTION

PATENT NO. : 5,519,049

DATED : May 21, 1996

INVENTOR(S) : ALAN A. NORRIS ET AL.

It is certified that error appears in the above-identified patent and that said Letters Patent is hereby corrected as shown below:

Column 3, line 7, "-12-12-" should be -- 12-[2 --.

Column 3, lines 20-21, "27-tetramethyl11,28-dioxa-" should be -- 27-tetramethyl-11,28-dioxa- --.

Column 3, lines 21-22, "18-ene2," should be -- 18-ene-2, --.

Column 3, line 25, "22.3.1.0$^{4,9}$]" should be -- [22.3.1.0$^{4,9}$] --.

Column 3, line 29, "22.3.1.0$^{4,9}$]" should be -- [22.3.1.0$^{4,9}$] --.

Column 4, line 46, "[FREON]" should be -- "FREON" --.

Column 6, lines 23-24, "thereof, and a pharmaceutically acceptable aerosol propellant." should be --thereof.--

Column 8, line 38, "aoetyloholine" should be --acetyloholine--.

Column 9, line 37, "J" should be --I--.

Column 12, lines 14-15, "4azatricyclo[[22.3.1.0$^{4,9}$octacos" should be -- 4-azatricyclo[22.3.1.0$^{4,9}$]octacos --.

Column 12, line 20, between "12-23", insert the following: --[2-(4-hydroxy-3-methoxycyclohexyl)-1-methylvinyl]- --.

UNITED STATES PATENT AND TRADEMARK OFFICE
CERTIFICATE OF CORRECTION

PATENT NO. : 5,519,049

DATED : May 21, 1996

INVENTOR(S) : Alan A. Norris et al.

It is certified that error appears in the above-identified patent and that said Letters Patent is hereby corrected as shown below:

Column 12, line 42, "claim 11" should be --claim 3--.

Signed and Sealed this

Third Day of September, 1996

BRUCE LEHMAN

*Attest:*

*Attesting Officer*  *Commissioner of Patents and Trademarks*